United States Patent [19]

Sablotsky et al.

[11] Patent Number: 4,994,278

[45] Date of Patent: Feb. 19, 1991

[54] BREATHABLE BACKING

[75] Inventors: Steven Sablotsky, Miami; Cheryl M. Gentile, Plantation, both of Fla.

[73] Assignee: Noven Pharmaceuticals, Inc., Miami, Fla.

[21] Appl. No.: 295,788

[22] Filed: Jan. 11, 1989

Related U.S. Application Data

[63] Continuation of Ser. No. 164,482, Mar. 4, 1988, Pat. No. 4,814,168.

[51] Int. Cl.$^5$ ............................................. A61F 13/00
[52] U.S. Cl. ................................. 424/449; 424/489; 424/447; 424/78
[58] Field of Search ................. 424/489, 448, 447, 78

[56] References Cited

U.S. PATENT DOCUMENTS

| | | |
|---|---|---|
| Re. 31,887 | 5/1985 | Hodgson . |
| 3,121,021 | 4/1960 | Copeland . |
| 3,214,501 | 10/1965 | Strauss . |
| 3,426,754 | 2/1969 | Blerenbaum et al. . |
| 3,580,254 | 5/1971 | Stuart . |
| 3,636,922 | 1/1972 | Ketner . |
| 3,867,939 | 2/1975 | Moore et al. . |
| 3,881,489 | 5/1975 | Hartwell . |
| 3,961,628 | 6/1976 | Arnold . |
| 4,069,307 | 1/1978 | Higuchi et al. . |
| 4,176,664 | 12/1979 | Kalish . |
| 4,336,243 | 6/1982 | Sanvordeker et al. . |
| 4,415,628 | 11/1983 | Cioca et al. . |
| 4,470,962 | 9/1984 | Keith et al. . |
| 4,478,596 | 10/1984 | Michelson . |
| 4,486,193 | 12/1984 | Shaw et al. . |
| 4,540,412 | 9/1985 | Van Overloop . |
| 4,559,938 | 12/1985 | Metcalfe et al. . |
| 4,561,435 | 12/1985 | McKnight et al. . |
| 4,573,996 | 3/1986 | Kwiatek et al. . |
| 4,585,797 | 4/1986 | Cioca . |
| 4,632,860 | 12/1986 | D'Antonio et al. . |
| 4,638,043 | 1/1987 | Szycher et al. ................... 428/489 |
| 4,638,797 | 1/1987 | Merrill et al. . |
| 4,649,909 | 3/1987 | Thompson . |
| 4,681,584 | 7/1987 | Gale et al. . |
| 4,686,137 | 8/1987 | Ward, Jr. et al. . |
| 4,751,087 | 6/1988 | Wick . |
| 4,753,231 | 6/1988 | Lang et al. . |
| 4,818,540 | 4/1989 | Chien et al. . |
| 4,832,009 | 5/1989 | Dillon . |
| 4,854,995 | 9/1989 | Kasper et al. . |
| 4,863,788 | 2/1989 | Bellairs et al. . |
| 4,871,611 | 6/1989 | LeBel . |
| 4,931,282 | 6/1990 | Asmus et al. ........................ 424/78 |

Primary Examiner—Merrell C. Cashion, Jr.
Assistant Examiner—Leon R. Horne
Attorney, Agent, or Firm—Sybil Meloy

[57] ABSTRACT

A composition comprising a flexible backing for a transdermal drug preparation with a water vapor transmission rate about equal to or in excess of that of ethylene vinyl alcohol copolymer, namely equal to or in excess of, at one mil thickness, of about 2 to 4 grams and more preferably in excess of 6 grams per 24 hours per 100 square inches at 40° C. and 90% relative humidity and an oxygen transmission rate equal to or less than ethylene vinyl alcohol copolymer, namely at one mil thickness equal to or less than about 0.01 to 0.1 cubic centimeters per 100 square inches measured over 24 hours at 1 atmospheric pressure, 20° C. and 65% relative humidity.

8 Claims, 1 Drawing Sheet

BREATHABLE BACKING

CROSS-REFERENCE TO RELATED APPLICATION

This application is a continuation in part of U.S. patent application Ser. No. 164,482, filed Mar. 4, 1988, now under U.S. Pat. No. 4,814,168, granted Mar. 21, 1989, which U.S. patent application Ser. No. 164,482 is incorporated herein by reference. Applications are assigned to Noven Pharmaceuticals, Inc. of Miami, Fla.

BACKGROUND OF THE INVENTION

This invention relates to a flexible backing for a composition for administration of drugs through the skin.

With increasing frequency, pharmacologically active agents have been administered by application to the skin, often in a solid carrier. The drug is incorporated into the carrier and attached to the skin, typically by means of an adhesive. The carrier can be a gel or a more rigid polymer or combination of polymeric substances and can have single or multiple components. The adhesive can also function as the carrier. One side of the carrier is applied to the skin, while the other side is accessible to the environment.

Typically, a backing is present on the side of the carrier accessible to the environment. The backing limits the passage of substances from the carrier into the environment, and limits the reverse passage of substances from the environment into the carrier. Typically, the backings are composed of metal foil, metallized plastic, or single or multiPle layers of a polymeric (plastic) substances which do not permit the passage of more than negligible amounts of water.

One known carrier, namely the Bolar Pharmaceutical Co. transdermal preparation for nitroglycerin sold under the trademark NTS, contains a backing material containing polyvinyl chloride. Other backing materials used in transdermal preparations marketed in the United States include aluminized polyester (Transderm Scopolamine, CIBA); other aluminized plastics are used in Transderm Nitro (CIBA); Deponit (Wyeth); and Catapress-TTS (Boehringer Ingelheim.). Aluminum foil (Nitro-Dur, Key; Nitrodisc, Searle), polyethylene/polyvinylidene chloride coextrusion (Nitro-Dur II, Key), and Polyester (Estraderm, CIBA) are also used.

Aluminum containing backing materials have negligible moisture vapor transmission rates. Aluminum foil, as reported in "Aluminum Foil" by the Aluminum Association, Inc., page 5, Table 3, Second Edition, January 1981, is impermeable to moisture at a thickness of one mil (0.001 inch) and thicker. The water vapor transmission rate is 0.02 grams or less/100 square inches in 24 hours at 100 degrees Fahrenheit (° F.) for a foil of 0.00035 inches, a commonly used thickness. When 0.00035 inch foil is laminated, the water vapor transmission rate drops to practically zero.

Other films common to the film industry, not necessarily to transdermals, which in principle are applicable to transdermals are polyethylene and ethylene copolymers, linear low density polyethylene, very low density polyethylene, ethylene methyl acrylate, ethylene vinyl acetate, polypropylene, polystyrene, polyurethane, polyvinyl and vinyl copolymers, and vinylidene chloride polymers and copolymers (Sarans).

Other available plastic films include:
Acetal
Acrylic
Acrylonitrile Butadiene Styrene (ABS)
Acrylonitrile (Methyl Methacrylate/MMA) Copolymer
Acrylonitrile Copolymer, Biaxially-Oriented
Acrylonitrile Types, Other
Ethylene Ethyl Acrylate (EEA)
Ethylene Methyl Acrylate (EMA)
Ethylene Vinyl Acetate (EVA)
Ethylene Vinyl Acetate (EVA) Copolymer
Ethylene Vinyl Alcohol (EVOH) Polymer
Ionomers
Nylon (Polyamide)
Nylon (Polyamide), Biaxially-Oriented
Nylon (Polyamide), Monoaxially-Oriented
Nylon (Polyamide) Copolymer
Polybutylene (PB)
Polycarbonate (PC)
Polyester
Polyester, Oriented
Polyester, Thermoplastic (Polyethylene TerePhthalate) (PET)
Polyester, Thermoplastic Copolymer (PET-G)
Polyethylene, High Density (HDPE)
Polyethylene, High Density (HDPE), Oriented
Polyethylene, High-Molecular-Weight, High Density (HMWHDPE)
Polyethylene, Intermediate-Molecular-Weight, High Density (IMWHDPE)
Polyethylene, Linear Low Density (LLDPE)
Polyethylene, Low Density (LDPE)
Polyethylene, Medium Density (MDPE)
Polyethylene Oxide
Polyimide
Polypropylene (PP)
Polypropylene (PP), Coated
Polypropylene, Oriented (OPP)
Polystyrene (PS)
Polyurethane (PU)
Polyvinyl Acetate (PVAC)
Polyvinyl Chloride (PVC)
Polyvinylidene Chloride (PVDC)
Styrene Acrylonitrile (SAN)

Backings previously used for transdermal compositions typically consist of a polymer alone or laminated to a metal foil which is substantially impervious to moisture and gas, and thus not "breathable" in the sense of permitting permeation of water vapor to and from the composition. The result of this lack of breathability is a tendency of the formulation to irritate the skin or to tend to detach from the skin or both.

The backing must be sufficiently flexible to permit movement of the skin and be compatible with the carrier and drug in the sense that the carrier or the drug does not substantially degrade the backing, especially under normal conditions of use and storage for one to two years. The backing should also not substantially degrade the drug or the carrier.

The general theory of permeation of a gas or a liquid through a polymer matrix is that permeation is a product of the diffusion time and solubility constant of the permeant in the polymer matrix, both of which are often independent of each other. Very often, the property which results in a good gas barrier results in a poor water barrier. For example, highly polar polymers such as those containing hydroxyl groups (ethylene vinyl alcohol) are excellent gas barriers but poor water barriers. Conversely, non-polar hydrocarbon polymers such as polyethylene have excellent water barrier properties but poor gas barrier properties.

In order to be a good barrier polymer, the material should have some degree of polarity, chain stiffness, inertness, close chain-to-chain packing, some bonding or attraction between chains and a high glass transition temPerature (Tg). The various types of barrier polymers and their uses are thoroughly discussed in Salame, et al., "Barrier Polymers", Polym.-Plast. Technol. Eng. 8(2), 155-175 (1977). Not only does the functional group have an effect on oxygen permeability, but so does the degree of crystallinity, the degree of orientation of Polymer Chains, the inclusion of fillers and additives and the presence of moisture in the polymer. As a rule of thumb, permeation increases by 30 to 50% for every 5 degrees Celsius (C°) temperature rise. Rate of permeation is also affected by the molecule, the molecular shape and the polarity of the permeating species.

SUMMARY OF THE INVENTION

It has now been found that a backing for use with a transdermal composition can be constructed such that not only is the backing compatible with the drug/carrier composition and the drug/carrier composition is compatible with the drug, but the backing permits the passage of water vapor without permitting the passage of the drug or gases from the composition or the entry of gases or liquids from the environment.

The backing material of this invention comprises at least one, and can contain two or more layers. At least one layer of the backing is a membrane which is compatible with the drug chosen and with which the drug is compatible, is flexible, and has a water vapor transmission rate about equal to or in excess of that of ethylene vinyl alcohol copolymer (EVOH) of about 0.2 to 3 mil thickness. EVOH at 1 mil thickness has a water vapor transmission rate in excess of about 2 to 4 g/100 square inches (in$^2$) per 24 hours, at 40° C. and 90% relative humidity (RH).

The backing also should have an oxygen transmission rate about equal to or less than that of EVOH of about 0.2 to 3 mil thickness. EVOH at 1 mil thickness has an oxygen transmission rate of about 0.01 to 0.1 cubic centimeters per 100 square inches measured over 24 hours at one atmosphere pressure, at 20° C. and 65% relative humidity.

The additional layers of the breathable backing have water vapor transmission rates equal to or in excess of that of EVOH of 0.2 to 3 mil thickness, more preferably in excess of about 6 grams and even more preferably in excess of about 9 grams per 100 in$^2$ per 24 hours at 40° C. and 90% RH.

Some of the backing materials of this invention, for example nylon/ethylene vinyl alcohol/polyethylene coextrusions have been used in high barrier food packaging applications. In those compositions, the nylon and polyethylene tend to reduce the adverse effect of moisture on the very low gas transmission properties of EVOH, while enhancing flex crack-resistance, strength and toughness of the composition, to result in a clear film having low gas barrier properties throughout the range of relative humidity found in ambient conditions of food storage

DETAILED DESCRIPTION OF THE INVENTION

Figure 1:
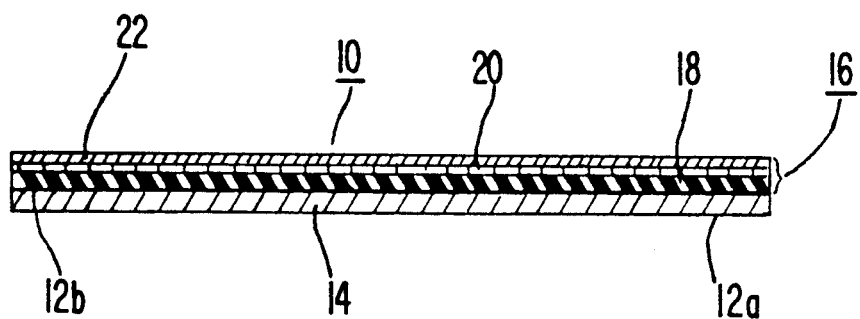
FIG. 1 is a cross-section of the transdermal composition having the backing material of this invention.

A composition for the administration of drugs through the skin comprising a pharmacologically active agent in a transdermal carrier, namely one suitable for transdermal administration, and a backing for the carrier.

The backing comprises at least one layer, said primary layer having a high water vapor transmission rate and a moderate to low gas transmission rate. Thus the backing has a water vapor transmission rate about equal to or in excess of that of ethylene vinyl alcohol copolymer (EVOH) and a gas transmission rate about equal to or less than EVOH, in which the EVOH is of about 0.2 to 3 mil thickness. The backing can comprise additional polymeric layers, for example, a second layer having a high water vapor transmission rate, as well as additional layers. The additional layers can be placed on one or both sides of the first layer.

Basically, the backing material is constructed of a barrier Polymer or resin or other permeable material. The term "barrier" is used here in reference to a material's resistance to absorption, diffusion, and desorption of gases, moisture and other chemicals. By the use of certain barrier materials, a film can be made selectively permeable to water or other liquid vapor rather than gas or vice versa.

The permeability to gas and moisture vapor is known or can be computed using standardized tests. A comparison of different plastics is found in "Barrier Resins Key New Package Development", Plastics Packaging, July/August 1988, pp. 17-21.

TABLE 1

| Comparison of Barrier Properties for Commercial polymers | | |
|---|---|---|
| | Oxygen Transmission Rate 25° C., 65/RH (cc-mil/100 in$^2$ —24 hours) | Moisture Vapor Transmission Rate, 40° C., 90/RH (cc-mil/100 in$^2$ —2 hours) |
| Ethylene vinyl alcohol | 0.05 to 0.18 | 1.4 to 5.4 |
| Polyvinylidene chloride | 0.15 to 0.90 | 0.1 to 0.2 |
| Acrylonitrile | 0.80 | 5.0 |
| Amorphous nylon | 0.74 to 2.0 | |
| Oriented polyester terephthalate | 2.60 | 1.2 |
| Oriented nylon | 2.10 | 9.0 |
| Rigid polyvinyl chloride | 14.0 | 3.0 |
| Low density polyethylene | 420 | 1.0 to 1.5 |
| High density polyethylene | 150 | 0.4 |
| Polypropylene | 150 | 0.69 |
| Polystyrene | 350 | 7 to 10 |

In the above table, oxygen transmission rate is expressed in cubic centimeters of oxygen of 1 mil film per 100 square inches surface area per 24 hours at 65% relative humidity (RH) and 25° Celsius (° C.) and moisture vapor transmission rate is expressed in cubic centimeters per 100 square inches of surface area of 1 mil film per 24 hours at 40 degrees Celsius (° C.) and 90% relative humidity Additional moisture vapor transmission rates, reported in the EVALCA bulletin number 110, are:

TABLE 2

| Material | Moisture Vapor Transmission Rate (40° C./90% R.H.) | |
| --- | --- | --- |
| | g. 30 microns/ m²/24 Hrs. | g. mil/100 in²/24 Hrs. |
| Biaxially Oriented Polypropylene | 5 | 0.38 |
| High Density Polyethylene | 5 | 0.38 |
| Polypropylene | 9 | 0.69 |
| Low Density Polyethylene | 15 | 1.14 |
| Biaxially Oriented Polyester Terephthalate | 15 | 1.2 |
| Rigid Polyvinyl Chloride | 40 | 3.1 |
| Polystyrene | 112 | 8.5 |
| Biaxially Oriented Nylon 6 | 134 | 10.0 |
| Polycarbonate | 14.5 | 1.1 |
| EVAL EP-F | 50 | 3.8 |
| EVAL EP-H | 28 | 2.1 |
| EVAL EP-K | 28 | 2.1 |
| EVAL EP-E | 19 | 1.4 |
| EVAL EP-G | 19 | 1.4 |
| Saran 5253 PVC | 3 | 0.22 |
| Barex 210 Nitrile | 80 | 6.1 |

In the above table in² refers to square inches and m² to square meters.

The backing should:

1. Maintain its physical and chemical integrity in the environment of use;
2. Provide mechanical support for the other laminae forming a laminate carrier;
3. Be substantially impermeable to the pharmacological agent;
4. Be selectively permeable to the passage of internal water vapor; and
5. Be substantially impermeable to gases to water or moisture but permeable to water vapor.

The molecular weight of the polymers selected for the backing are such that the backing has the foregoing characteristics and the layers, the indicated water vapor and oxygen transmission rates.

The term "pharmacologically active agent" or "drug", as used herein, means and refers to any substance capable of being administered to the skin of an animal to exert a local or systemic effect. Currently, nitroglycerin, estradiol, scopolamine and clonidine are available commercially in transdermal formulations. However, in theory, any drug is capable of being used locally or systemically by application to the skin. Thus, the term "pharmaceutically active agent" can include, but is not limited to:

1. Anti-infectives, such as antibiotics, including penicillin, tetracycline, chloramphenicol, sulfacetamide, sulfamethazine, sulfadiazine, sulfamerazine, sulfamethizole and sulfisoxazole; antivirals, including idoxuridine; and other anti-infectives including nitrofurazone and the like;
2. Anti-allergenics such as antazoline, methapyrilene, chlorpheniramine, pyrilamine and prophenpyridamine;
3. Anti-inflammatories such as hydrocortisone, cortisone, dexamethasone, fluocinolone, triamcinolone, medrysone, prednisolone, and the like;
4. Decongestants such as phenylephrine, naphazoline, and tetrahydrozoline;
5. Miotics and antichlolinesterases such as pilocarpine, carbachol, and the like;
6. Mydriatics such as atropine, cyclopentolate, homatropine, scopolamine, tropicamide, ecuatropine and hydroxyamphetamine;
7. Sympathomimetics such as epinephrine;
8. Beta-adrenergic agents such as salbutamol and terbutaline.
9 Sedatives, hypnotics and anesthetics such as chloral, pentobarbital, phenobarbital, secobarbital, codeine, (alpha-bromoisovaleryl) urea, lidocaine, fentanyl and fentanyl analogs, opiates, opioids, agonists and antagonists therefor;
10. Psychic energizers such as 3(2-aminopropyl)indole, 3(2-aminobutyl) indole, and the like;
11. Tranquilizers such as reserpine, chlorpromazine, thiopropazate and benzodiazepines such as alprazolam, triazolam, lorazepam and diazepam;
12. Androgenic steroids such as methyltestosterone and fluoxymesterone;
13. Estrogens such as estrone, 17-beta-estradiol, ethinyl estradiol, and diethylstilbestrol;
14. Progestational agents, such as progesterone, 19-norprogesterone, norethindrone, megestrol, melengestrol, chlormadinone, ethisterone, medroxyprogesterone, norethynodrel and 17 alpha-hydroxyprogesterone;
15 Humoral agents such as the prostaglandins, for example $PGE_1$, $PGE_{2alpha}$, and $PGF_{2alpha}$;
16. Antipyretics such as aspirin, salicylamide, and the like;
17. Antispasmodics such as atropine, methantheline, papaverine, and methscopolamine;
18. Anti-malarials such as the 4-aminoquinolines, alpha-aminoquinolines, chloroquine, and pyrimethamine;
19. Antihistamines such as diphenhydramine, dimenhydrinate, perphenazine, and chloropenazine;
20. Cardioactive agents such as nitroglycerin, isosorbide dinitrate, isosorbide mononitrate, quinidine sulfate, procainamide, benzydroflumethiazide, flumethiazide, chlorothiazide, calcium antagonists such as nifedipine, verapamil and diltiazem and selective and non-selective beta blockers such as timolol and propranolol, ACE inhibitors such as captopril and various other agents such as clonidine and prazosin.
21. Nutritional agents such as essential amino acids and essential fats.

Other drugs having the same or different physiological activity as those recited above can be employed in drug delivery devices within the scope of the present invention.

Drugs, contained in the carrier, can be in different forms, such as uncharged molecules, components of molecular complexes or pharmacologically acceptable salts or derivatives thereof. Simple derivatives of the drugs such as pharmaceutically acceptable ethers, esters, amides, and the like which have desirable retention and release characteristics but which are easily hydrolyzed at body pH, enzymes, pro-active forms, and the like can be employed.

The dosage unit amount for conventional beneficial drugs as set forth herein, in the accompanying disclosure and examples, is also known to the art in standard reference books such as Remington's Pharmaceutical Sciences, Seventeenth Edition, Part IV, 1970, published by Mack Publishing Co., Easton, Pa. and Goodman and Gilman, "The Pharmacological Basis of Therapeutics", MacMillan Publishing Co., 6th Edition (1980).

"Transdermal carrier", as used herein, means and refers to any generally planar carrier suitable for containing a pharmaceutically active agent for transdermal administration having two surfaces, one surface being adapted for application to the skin and the second surface being opposed thereto. A great number of materials are known in the prior art for such uses. The nature of the material is not critical so long as the carrier permits release of the drug on to and through the skin, as in the case of transdermal administration. Typical transdermal carriers include pressure sensitive adhesives, such as polyacrylic acids, natural and synthetic rubbers, silicones, and polyvinyl acetates. One surface of the carrier is adapted for application to the skin. The other surface carries the backing material.

Suitable polymeric materials for the transdermal backing include acrylonitrile, cellulose acetate, polycarbonate, ethylene vinyl acetate, ethylene methyl acrylate, polyester, polyethylene, polypropylene, polystyrene, polyurethane, polyvinyl alcohol, ethylene vinyl alcohol, polyamides, polyvinylidene Chloride and polyvinyl chloride. Some polymers increase barrier properties by orienting the polymer chains in one or two directions.

The backing material of this invention comprises at least one, and can contain two or more natural or synthetic polymeric layers. At least one layer of the backing is composed of a polymer which is compatible with the drug chosen and with which the drug is compatible, is flexible, and has a water vapor transmission rate equal to or greater than EVOH of 0.2 to 3 mil thickness, namely a rate equal to or in excess of about 2 to 4 grams/100 in$^2$ per 24 hours, at 40° C. and 90% RH and more preferably 6 grams and an oxygen transmission rate equal to or less than EVOH of 0.2 to 3 mil thickness, namely of less than 0.01 to 0.1 cubic centimeters per 100 square inch when measured over 24 hours at one atmosphere pressure, 20° C. and 65% relative humidity.

The backing can also have a second or additional layers composed of a polymer which is compatible with the drug chosen and with which the drug is compatible, is flexible, and has a water vapor transmission rate in excess of that of EVOH of 0.2 to 3 mil thickness, namely in excess of about 2 to 4 grams per 100 square inches per 24 hours, at 40° C. and 90% relative humidity and preferably in excess of 6 grams.

The water vapor transmission rate of a given polymer is a function of the polymer and thus varies with the average molecular weight, configuration and orientation, chain length, nature of repeating units, the degree of crosslinking, the degree of crystallinity, the nature and extent of the monomer and the like, as well as time, temperature, relative humidity and thickness of the film. The rate thus varies, not only from polymer to polymer, but to different types of a specific polymer.

The preferred polymers for the additional layers are those having the greater water vapor transmission rate, thus the preferred polymers are cellulose acetate, nylon, polycarbonate, acrylonitrile, polystyrene, polyurethane and polyvinyl alcohol, or copolymers or multipolymers of these plastics with additional monomers. Polyurethane is an especially preferred material for the secondary layer.

Thus, the breathable backing of this invention comprises at least one layer of a substance having a high water vapor transmission rate and a low gas transmission rate. These physical properties can be found in the highly polar polymers, such as those containing hydroxyl groups such as polyvinyl alcohol, and ethylene vinyl alcohol, see e g., Barrier Polymers article, 1977, p. 156. More particularly, ethylene vinyl alcohol copolymer (EVOH) has a particularly low gas transmission rate.

The backing material can consist of a single layer having the indicated high water vapor transmission rate and low gas transmission rate. In addition, a single or multi-layered material can be used on one or both sides of the primary layer. These secondary layers need only have the high water vapor transmission rate and can be used to minimize potential degradation of the primary layer by the presence of air and moisture. The substances selected for additional polymeric layers can be the same or of different polymers.

In general, the additional layers have a moisture vapor transmission rate in excess of that of EVOH of 0.2 to 3 mil thickness, namely in excess of about 2 to 4 grams per 100 square inches at 40° C., 90% relative humidity over 24 hours, and more preferably in excess of about 6 grams per 100 square inch and more preferably in excess of 9 grams per 100 square inch.

The backing can be prepared by any of the methods used to join plastics in a film, including lamination or coextrusion. In the case of lamination, various means known in the art can be utilized to cause the layers to adhere.

Typically, each layer of the laminate is approximately 5 to 100 microns, and preferably 12 to 75 microns in thickness.

The preferred backing material for use in this invention is a layer of ethylene vinyl alcohol copolymer laminated or coextruded with polyurethane. An especially preferred backing material for use in this invention is one in which the polyurethane film is that available from JPS Elastomerics, 395 pleasant Street, Northampton, Mass. 01061. The preferred ethylene vinyl alcohol copolymer is the polymer sold under the trademark "EVAL" item EF-F, available from EVAL Company of America, 1001 Warrenville Road, Suite 201, Lisle, Ill. 60532. The EF-F polymer has the following physical properties:

| Item | Unit | Measuring Method | Measuring Condition | EF-F | Range For All EVALS |
|---|---|---|---|---|---|
| Thickness | Microns | | | 15 | 12–25 |
| Tensile strength, MD | kg/mm$^2$ | JIS Z 7509 | 20° C. 65% RH | 9 | 7–21 |
| (Breaking) TD | | | | | 4–20 |
| Elongation, MD | % | JIS Z 7509 | 20° C. 65% RH | 180 | 100–260 |
| (Breaking) TD | | | | 140 | 100–190 |
| Water vapor transmission rate | g/m$^2$-24 hrs | JIS Z 0208 | 40° C. 90% RH | 100 | 35–100 |
| Water absorption | % | | 30° C. 24 hrs | 8.6 | 5.9–8.6 |
| Equilibrium moisture absorption | % | | 20° C. 65% RH | 3.9 | 2.8–3.9 |
| Dimensional MD stability under TD heat | % | | 140° C. 1 hr | −2.7 −0.9 | (−1.6) − (−4.0) (−0.5) − (+1.4) |
| Oxygen transmission | cc/m$^2$- | JIS Z 1707 | 35° C. 0% RH | 0.5 | 0.4–3.2 |

| Item | Unit | Measuring Method | Measuring Condition | EF-F | Range For All EVALS |
|------|------|------------------|---------------------|------|---------------------|
| rate | 24 hrs-atm | | 20° C. 65% RH | 0.5 | 0.3–1.5 |
| | | | 20° C. 85% RH | 2 | 1–3.3 |
| | | | 20° C. 100% RH | 25 | 6–25 |
| Melting point | ° C. | | | 181 | 164–181 |

In the foregoing table and elsewhere in this application, the following standard abbreviations are used: kilograms (kg), millimeters (mm), square millimeters (mm$^2$), grams (g), centimeters (cm), square centimeters (cm$^2$), cubic centimeters (cc), meters (m), square meters (m$^2$), percent (%), atmospheric pressure (atm), degrees Celsius (° C.), relative humidity (RH), machine direction (MD) and transverse direction (TD). JIS refers to Japanese Industrial Standards.

The layers are juxtaposed face to face, and are bonded to each other. They are sufficiently flexible to be able to adapt to the contour of the skin and movements therein.

It is known that the mole percent ethylene in an ethylene vinyl alcohol copolymer affects not only the oxygen transmission rate of the copolymer, but the sensitivity of that oxygen transmission rate to relative humidity. Thus, the lower the percentage of ethylene in ethylene vinyl alcohol copolymer, the lower the oxygen transmission rate. Thus, it has been reported that a 1.0 mil ethylene vinyl alcohol copolymer containing 29 mole percent ethylene has an oxygen transmission rate of less than 0.02 at 0% relative humidity and 68° F, and approximately 0.05 at 80% relative humidity. On the other hand, under the same conditions of relative humidity and temperature, ethylene vinyl alcohol copolymer containing 38 mole percent and 44 mole percent of ethylene has an oxygen transmission rate of about 0.06 to 0.07 at 0% relative humidity, rising to approximately 0.2% at 80% relative humidity. In contrast, a 1.0 mil nylon film has an oxygen transmission rate of just above 2 at relative humidities ranging from 0% to in excess of 80% at 73° F. Similarly, the coextrusion of an ethylene vinyl alcohol copolymer and nylon tends to lower the oxygen transmission rate through a wide range of relative humidities, as compared with the non-coextruded ethylene vinyl alcohol copolymer.

The following examples illustrate the invention more fully without any intention of being limited thereby.

Moisture Vapor Transmission Rate ("MVTR"0 ) and Oxygen Transmission Rate ("OTR") for Films Used in the Examples

| Material | MVTR grams/ 100 in$^2$/24 hrs. | OTR cc/100 in$^2$/24 hrs. |
|----------|-------------------------------|--------------------------|
| EVAL EF-F: (15 microns) | 6.45 (40° C., 90% RH) | 0.03 (20° C., 65% RH) 0.13 (20° C., 85% RH) |
| Urethane: (38 microns) (76 microns) | 20.0 (20° C.) 10.0 (20° C.) | — — |
| Nylon, biaxially oriented (25 microns) | 9–10 (40° C., 90% RH) | 1.3–2.3 (25° C., atm) dry |

BACKING MATERIALS

EXAMPLE 1

A backing for a transdermal drug delivery system was prepared as follows: first, a 1.5 mil polyurethane was laminated to a 15 micron ethylene vinyl alcohol film with a polyurethane based adhesive using a Dru-Tec Laminator. Next, the remaining exposed ethylene vinyl alcohol film was laminated to a 1.0 mil polyurethane with a polyurethane based adhesive on the Dru-Tec Laminator.

EXAMPLE 2

Following the procedure in Example 1, a 1.5 mil polyurethane on both sides of the 15 micron ethylene vinyl alcohol film was prepared.

EXAMPLE 3

Following the procedure in Example 1, a 1.5 mil polyurethane on one side of the 15 micron ethylene vinyl alcohol film and a 1.0 mil nylon on the other side was prepared.

EXAMPLE 4

Following the procedure in Example 1, a 1.5 mil polyurethane on one side of the 15 micron ethylene vinyl alcohol film and 0.7 mil ethylene methyl acrylate on the other side was prepared.

EXAMPLE 5

Following the procedure in Example 1, a 1.5 mil polyurethane on one side of the 15 micron ethylene vinyl alcohol film and 3.0 mil polyurethane on the other side was prepared.

EXAMPLE 6

Following the procedure in Example 1, a 1.0 mil nylon on one side of the 15 micron ethylene vinyl alcohol film and 0.7 mil ethylene methyl acrylate on the other side was prepared.

EXAMPLE 7

Following the procedure in Example 1, a 1.0 mil nylon on only one side of the 15 micron ethylene vinyl alcohol film was prepared.

EXAMPLE 8

Following the procedure in Example 1, a 0.7 mil polyurethane film on one side of the 15 micron ethylene vinyl alcohol film and a 1.0 mil polyurethane on the other side was prepared.

EXAMPLE 9

Following the procedure in Example 1, a 0.7 mil ethylene methyl acetate on both sides of the ethylene vinyl alcohol film was prepared.

EXAMPLE 10

Following Example 1, a co-extrusion was prepared.

EXAMPLE 11

To an adhesive composition is applied a backing material in any wearable shape of 1-200 cm² surface area and having a thickness of 12 to 175 microns. The backing material is composed of one or more polymeric layers, joined by any conventional or known means of layering including, but not limited to, lamination, spraying, coating, condensation or coextrusion. The backing is joined to one side of the adhesive transdermal composition.

To release the drug, the preparation is applied to the skin.

EXAMPLE 12

By the method of Example 1, backings, either laminated or coextruded, having 1, 2, 3 or more layers can be prepared as follows:

| layer against adhesive | layer 2 | layer 3 |
|---|---|---|
| EVAL EF-F | — | — |
| EVAL EF-F | Polyurethane | — |
| Polyurethane | EVAL EF-F | — |
| Polyurethane | EVAL EF-F | Polyurethane |
| Nylon | EVAL EF-F | — |
| EVAL EF-F | Nylon | — |
| Nylon | EVAL EF-F | Polyurethane |
| Ethylene Methyl Acrylate (EMA) | EVAL EF-F | — |
| EVAL EF-F | EMA | — |
| EMA | EVAL EF-F | Polyurethane |

Wherein the term "EVAL EF-F" refers to a preparation having a thickness of 10 to 25 microns, the polyurethane has a thickness of 5 to 76 microns, the nylon has a thickness of 10 to 51 microns, the EMA has a thickness of 10 to 51 microns.

DETAILED DESCRIPTION OF THE DRAWING

The composition containing the backing in FIG. 1, which composition is generally shown by 10, is comprised of the drug containing carrier layer 14 having the face 12a to be applied to the skin containing an adhesive for adhering to the skin, and containing a second opposed layer 12b which is attached to the backing 16. The backing 16 shown in FIG. 1 consists of three layers 18, 20 and 22. The optional first layer 18 is the layer where the polymeric material has a high water vapor transmission rate. Intermediate layer 20 is the layer having both a high water vapor transmission rate and a low gas transmission rate, while a third layer 22 is the layer having a high water vapor transmission rate. The optional layer 18 minimizes the passage of the drug contained in matrix 14 to the backing layer, but permits the passage of moisture therefrom. Layer 20 also permits the passage of water vapor but substantially prevents the passage of drug, thus, maintaining the drug within the matrix 14. The optional layer 22 again permits the passage of water vapor to the environment, but by virtue of layer 20 limits access of gas from the environment through the device.

What is claimed is:

1. A composition, which comprises:
   a pharmacologically active agent in a transdermal carrier having two surfaces, one surface being adapted for application to the skin and a second surface opposed thereto; and
   a backing of at least a first layer of a plastic film for said second surface of the carrier, having a thickness from about 0.2 to 3 mils, and having a water vapor transmission rate at 1 mil thickness in excess of about 2 grams per 100 square inches per 24 hours, at 40° C. and 90% relative humidity and an oxygen transmission rate at 1 mil thickness equal to or less than 0.1 cubic centimeters per 100 square inches measured over 24 hours at 1 atmosphere of pressure, at 20° C. and 65% relative humidity, said backing having a first side facing the second surface of the transdermal carrier and a second side opposite thereto.

2. The composition of claim 1, in which the backing has a water vapor transmission rate in excess of 2 to 4 grams per 24 hours per 100 square inches at 40°C. and 90% relative humidity.

3. The composition of claim 2, in which said backing has a second layer in contact with said first second side of said backing having a water vapor transmission rate in excess of about 6 grams per 100 square inches per 24 hours at 40° C. and 90% relative humidity.

4. The composition of claim 3, in which the second layer of the backing has a water vapor transmission rate equal to or in excess of about 6 grams per 24 hours per 100 square inches, at 40° C. and at 90% relative humidity.

5. The composition of claim 3, having a third layer in said backing adjacent the second layer said backing having a water vapor transmission rate in excess of about 6 grams per 100 inches square for 24 hours at 40° C. and 90% relative humidity.

6. The composition of claim 5, in which said second and third layers have water vapor transmission rates in excess of 9 grams per 24 hours per 100 square inches at 40° C. and 90% relative humidity.

7. The composition of claim 2, in which the backing is ethylene vinyl alcohol copolymer having a water vapor transmission rate in excess of about 6 grams per 24 hours per 100 inches at 40° C. and 90% relative humidity and an oxygen transmission rate below about 0.1 cubic centimeters per 100 square inches per 24 hours at 1 atmosphere pressure, 20° C., and 65% relative humidity and a second layer of a polyurethane, having a water vapor transmission rate in excess of 6 grams under said conditions.

8. The composition of claim 7, having a third layer of polyurethane having a water vapor transmission rate in excess of 9 grams per 24 hours per inch at 40° C. and 90% relative humidity.

* * * * *